United States Patent [19]

Sherif

[11] Patent Number: 5,169,969

[45] Date of Patent: Dec. 8, 1992

[54] PROCESS FOR FORMING MIXED BIMETAL ALKOXIDE-CARBOXYLATE COMPOSITION AND NOVEL COMPOSITIONS THEREOF

[75] Inventor: Fawzy G. Sherif, Stony Point, N.Y.

[73] Assignee: Akzo nv, Arnhem, Netherlands

[21] Appl. No.: 732,555

[22] Filed: Jul. 19, 1991

Related U.S. Application Data

[63] Continuation-in-part of Ser. No. 534,824, Jun. 7, 1990, and a continuation-in-part of Ser. No. 552,633, Jul. 13, 1990.

[51] Int. Cl.$^5$ ............................ C07F 7/00; C07F 5/00
[52] U.S. Cl. ........................................ 556/28; 556/27; 556/54
[58] Field of Search .................... 556/54, 28, 27, 2, 1; 505/1

[56] References Cited

U.S. PATENT DOCUMENTS

| | | | |
|---|---|---|---|
| 3,432,445 | 3/1969 | Osgan et al. | 260/2 |
| 4,609,755 | 9/1986 | Farrar | 556/54 X |
| 4,681,959 | 7/1987 | Ayen et al. | 556/54 |
| 5,001,110 | 3/1991 | Nonaka et al. | 505/1 |
| 5,006,508 | 4/1991 | Treacy et al. | 505/1 |
| 5,075,284 | 12/1991 | Yamazaki | 505/1 |

FOREIGN PATENT DOCUMENTS 0296541 9/1988 Japan.

OTHER PUBLICATIONS

Osgan et al., "Prep. of Bimetallic-Oxo-Alkoxides", *Polymer Letters*, vol. 88, pp. 319–321 (1970).

*Primary Examiner*—Arthur C. Prescott
*Attorney, Agent, or Firm*—Richard P. Fennelly; Louis A. Morris

[57] ABSTRACT

Mixed bimetallic alkoxide-caraboxylate compositions are formed by reaction of at least two metal alkoxides and a carboxylic acid with elimination of distillable ester by-product therefrom. Hydrolysis of said compositions produce bimetallic hydroxy-carboxylates which, upon calcination, give bimetallic oxides.

13 Claims, No Drawings

PROCESS FOR FORMING MIXED BIMETAL ALKOXIDE-CARBOXYLATE COMPOSITION AND NOVEL COMPOSITIONS THEREOF

This is a continuation-in-part of U.S. Ser. Nos. 534,824 and 552,633, filed Jun. 7, 1990 and Jul. 13, 1990, respectively.

BACKGROUND OF THE INVENTION

It is known from U.S. Pat. No. 4,507,245 to react a rare earth metal alkoxide and an alkali metal alkoxide in an inert organic solvent under anhydrous conditions to yield a rare earth alkoxide of the formula $(MOR)_3$ where M is a rare earth metal and R is an alkyl group. Such alkoxides contain a single metal atom.

Certain disclosures also exist in the art in regard to producing products containing a metal atom, alkoxide moieties and the trimethylsilyl moiety ($R_3SiO$). Such products are formed by reacting a metal alkoxide with the covalent compound trimethylacetoxysilane and are disclosed in D. C. Bradley, J. Chem. Soc., 3404–3411 (1957); P. P. Sharma et al., Indian J. Chem., Vol. 5, September 1967, 456–457; R. C. Mehrotra et al., J. Indian Chem. Soc., Vol. 44, No. 3, 1967, pp. 223–224; R. C. Mehrotra et al., J. Indian Chem. Soc., Vol. 44, No. 4, 1967, pp. 345–346; and J. M. Batwara et al., J. Inorg. Nucl. Chem., 1970, Vol. 32, pp. 411–415.

Aluminum sec-butoxide was reacted with acetic acid as described by A. Ayral et al., J. Mater. Res., Vol. 4, No. 4, 1989, pp. 967–971. Sec-butyl alcohol was detected as a product initially, followed by sec-butyl acetate ester. This led the authors to propose an intermediate structure containing aluminum monobutoxide-diacetate which formed a basic acetate upon hydrolysis. Titanium (IV) butoxide was reacted with glacial acetic acid to obtain a titanyl-acrylate-type precursor, Ti n-$(OBu)_3(OAc)$, with the liberation of butanol. The chemical reactivity of the precursor was less than the parent alkoxide as claimed by C. Sanchez et al. in "Ultrastructure Processing of Advanced Ceramics", J. D. Mackenzie and D. R. Ulrich, eds., Wiley, New York, 1988, p. 77. Upon hydrolysis with water, the butoxide was removed while the acetate remained bonded to the titanium. In both cases, the authors did not separate or identify the intermediate they produced. This disclosure relates to use of a single alkoxide reagent.

Other condensation products have been reported (i.e., in U.S. Pat. No. 2,621,193) where titanium alkoxides are reacted with organic acids to get mixed alkoxide-carboxylate compositions of a single metal, for example, titanium.

U.S. Pat. No. 4,122,107 to J. F, Kenney discloses catalysts which are the reaction products of specific antimony or zirconium (IV) compounds with a carboxylate of calcium, manganese or zinc and an acid anhydride, alcohol, or glycol. Col. 3, lines 46–47 indicate that the product is a bimetallic alkoxide "or" carboxylate. Bimetallic alkoxide-carboxylate compositions are not disclosed.

M. Osgan et al. in Polymer Letters, Vol. 88, pp. 319–321 (1970) describe previous work reported in U.S. Pat. No. 3,432,445 dealing with condensation products of certain bivalent metal compounds (e.g., zinc acetate) as catalysts and trivalent metal compounds (e.g., aluminum alcoholates) and indicate that the proposed species (i.e., mu-oxo-alkoxides of aluminum and zinc) were not formed but that the condensation products contained some residual acetato groupings and some higher condensed species. Osgan et al. therefore proposed to form the desired condensation products by "some other independent way", namely, by the controlled hydrolysis of aluminum and zinc alkoxides under alcoholysis conditions.

In related U.S. Ser. Nos. 534,824 and 552,633 filed Jun. 7, 1990 and Jul. 13, 1990, respectively, mixed heavy bimetallic alkoxide-carboxylate compositions are formed which comprise reacting a heavy metal alkoxide and another heavy metal carboxylate under substantially anhydrous conditions with the elimination of distillable ester by-product therefrom. The products from this reaction can be used as a raw material for forming mixed metal oxides when fired. In cases in which a stable, isolated heavy metal carboxylate is not readily available, however, a need has arisen for a modified procedure to form such mixed alkoxide-carboxylate products. It is to this specific need that the present invention is addressed.

SUMMARY OF THE INVENTION

The instant invention relates to a novel process for forming novel mixed bimetal alkoxide-carboxylate compositions by reacting at least two heavy metal alkoxides and a carboxylic acid to form the desired mixed heavy metal alkoxide-carboxylate with elimination of distillable ester by-product therefrom. In essence, the present process results in the in situ formation of the carboxylate component of the desired product.

DETAILED DESCRIPTION OF THE INVENTION

The invention described below demonstrates that by reacting at least two metal alkoxides with a carboxylic acid, such as acetic acid, condensation of multimetal moieties in a mixed metal alkoxide-carboxylate product occurs with the liberation of an ester from the reaction mixture. Condensed metal-metal alkoxide-carboxylate compositions are formed. This molecularly uniform species contains two or more metals and is useful as a raw material for making uniform films and uniform electronic precursors for advanced ceramics. Upon hydrolysis, uniform bimetallic compositions useful for structural ceramics and powders for plasma spray coatings, for example, can be formed.

The metal alkoxide reagents can be selected from the metal dialkoxides, trialkoxides and tetraalkoxides. Representative dialkoxides include the magnesium alkoxides, strontium alkoxides and barium alkoxides. Representative trialkoxides include the alkoxides of aluminum, iron, chromium and the rare earth metals (scandium, yttrium, and the lanthanides). Representative tetraalkoxides include the alkoxides of zirconium, titanium and hafnium. The choice of which alkoxides to select will be governed by the identity of the metals desired in the mixed metal alkoxide-carboxylate product.

The carboxylic acid is reacted with the above alkoxide reagents, either with both in a one-step reaction or with one alkoxide just prior to reaction with the other alkoxide or alkoxides. The carboxylic acid used is preferably of the formula $R^1C(0)OH$, where $R^1$ is lower alkyl, most preferably acetic acid. This carboxylic acid reagent is to be used when the carboxylates of one or more of the desired metals is not sufficiently stable to serve as a reagent thereby necessitating its formation in situ in the presence of the metals or by its reaction with one of the metal alkoxides followed by reaction with the other(s).

The aforementioned alkoxide reagent and carboxylic acid can be reacted together under anhydrous conditions (e.g., in a substantially anhydrous organic solvent) at molar ratios of about 1:10 to about 10:1 at temperatures of from about 20° C. to about 120° C. with elimination of distillable ester by-product (e.g., acetate by-product) therefrom. The reaction which results in the elimination of the ester by-product is not a reversible reaction so there is no need to remove the by-product by distillation. However, if desired, a distillation step to remove the ester by-product can be used.

A preferred embodiment of the present invention involves selection of a metal trialkoxide and tetraalkoxide combination to give compositions containing a tetravalent metal (such as zirconium, titanium, hafnium and the like) and a trivalent metal (such as aluminum, iron, chromium, scandium, yttrium, the lanthanides and the like). In some cases the tetravalent alkoxide, e.g., zirconium tetraalkoxide, can be prereacted with a trivalent metal carboxylate, such as yttrium triacetate, whereby the trivalent metal acts as a desirable additive, e.g., a stabilizer, in the final composition. After this initial linking of the trivalent metal with tetravalent metal additional trivalent alkoxide can be used.

The reaction in accordance with the various preferred embodiments of the present invention described above can advantageously be initially carried out so that the trivalent and tetravalent metal precursors thereof give a final composition (after hydrolysis) containing a maximum of about 90%–96% by weight of $MO_2$ and at least 4%14 10% by weight of $M^1_2O_3$. Exemplary compositions are zirconia-alumina stabilized oxides. Such stabilized oxides are suitable as both thermally and wear resistant material for coatings. A preferred coating contains 4% yttria, 50% zirconia and 44% $Al_2O_3$ and is a suitable powder containing nontransformable tetragonal zirconia recommended for plasma spray coating applications.

This invention also demonstrated that by reacting a tetravalent metal alkoxide with a trivalent metal alkoxide in a molar ratio of 1:2 in the presence of an acid, condensation of the two metal species occurred. In addition, the loss of one or more alkoxide groups with one or more carboxylates from the acid formed one mole of an alkoxy-carboxylate ester which was eliminated from the reaction mixture. Determination of the quantity of this eliminated ester allowed for balancing of the reaction. Furthermore, extra alkoxide groups decomposed to olefins. Thus, a novel compound of the 1:2 reactants, where the ratio of M to $M^1$ is 1:2 was left behind (where M and $M^1$ are different metals of the type previously described and R and $R^1$ are alkyl, e.g., $C_1$–$C_4$ alkyl).

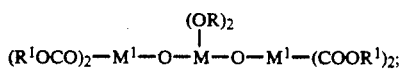

where the ratio of alkoxide to carboxylate is 1:2. While chemical analysis of the products indicates that the above structures are generally valid, the exact structures are not precisely known in every detail. The compositions achieved appear to depend upon the ratio of the alkoxide to carboxylate. It is probable that the reaction product contains the above compositions (as appropriate) in addition to higher condensed forms of such compositions.

The reaction can be represented as follows for zirconium n-butoxide and aluminum sec-butoxide:

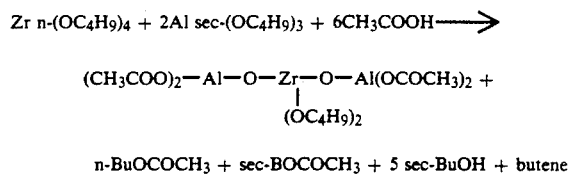

The raw material used for the tetravalent alkoxide can be an alkoxide alcohol complex such as M(OR)$_4$ROH which is a commercially available product. In this case, in addition to the separated ester as described above, one mole of alcohol for every mole of metal alkoxide can be distilled therefrom. The ester-alcohol usually forms an isotrope and can be distilled off at a slightly lower temperature than when using the alkoxide without the alcohol.

The compound formed and described above in connection with the 1:2 reaction can be further hydrolyzed, as shown in Example 6 to yield a basic acetate. If desired, this can be extrapolated to other metal moieties M and $M^1$ as those terms are earlier described.

Upon firing of the above compositions a mixed metal oxide is formed, with liberation of water, alcohol and organic combustion by-products, to yield a substantially chemically uniform oxide having the following repeat unit:

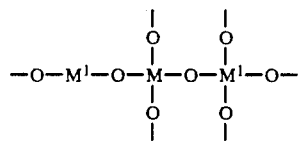

where the ratio of $M^1$ to M can range from about 1:10 to about 10:1. Intermediate firing showed the presence of one oxide as a uniform solid solution in the second oxide. The solid solution was indicated by the shift in the x-ray diffraction peaks of the second oxide and the absence of peaks of the first oxide.

The present invention is further illustrated by the Examples which follow.

EXAMPLE 1

This Example describes a Zr/Al precursor for preparing, in situ, a bimetallic oxide. Zirconium n-butoxide-butanol complex (114.3 gm, 0.25 mole), 129.5 gm of aluminum sec-butoxide (95%), 0.5 mole, and 90 gm (1.5 moles) of glacial acetic acid were mixed in a 5 liter round bottom flask. The mixture was heated slowly while stirring. When the temperature reached 132° C., 131 gm of liquid was distilled off. The residue was dried under vacuum using a rotary evaporator. More liquid was condensed in this step. It was mixed with the distillate, and the mixture was analyzed by gas chromatography (GC) and found to contain sec-butanol, sec-butyl acetate and n-butyl acetate. The weight of the residue was 124.9 gm which approaches 0.25 mole based on the formula of precursor I:

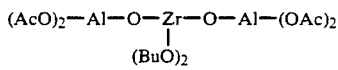

(AcO)₂—Al—O—Zr—O—Al—(OAc)₂　　(I)
　　　　　　　|
　　　　　(BuO)₂

The chemical composition of precursor (I) was demonstrated by elemental analysis as follows:

| Found %: | C = 34.62 | Calculated for (I): | C = 34.34 |
|---|---|---|---|
|  | H = 5.58 |  | H = 5.36 |
|  | Zr = 15.30 |  | Zr = 16.31 |
|  | Al = 9.80 |  | Al = 9.66 |

The infra red spectra of (I) showed a band of b 1575 cm$^{-1}$ wavelength characteristic of the acetate ion and two bands at 1135 and 1175 cm$^{-1}$ characteristic of butyl radical.

EXAMPLE 2

This Example demonstrates that addition of yttrium to an in situ Zr-Al system stabilizes the crystalline phase of the final $ZrO_2$ in $ZrO_2.Al_2O_3$ powder. Zirconium n-butoxide.butanol complex (325.7 gm, 0.75 mole) was combined with 19.2 gm of anhydrous yttrium acetate and Was heated to 130° C. until all the acetate dissolved Then, 162 cc acetic acid was added. A thick white material formed. To this was added, 110 cc of toluene, and the mixture Was stirred. Then, 380.92 gm (1.5 moles) of aluminum sec-butoxide and 1000 cc of toluene were added, and the mixture was refluxed for two hours. The white solid dissolved, and a clean solution was obtained. The solution was cooled to 50° C., and 270 cc of water was added. A gel was formed. The gel was broken and the resulting composition was stirred for one hour. The product was filtered, oven dried at 120° C. for two hours and was calcined at 1300° C. for two hours. The yield was 116.2 gm. The calcined powder was sieved to remove the −635 mesh particles. The bulk density of the classified powder was 1.9 g/cc. The flow was 1.6 cc/sec. Elemental analysis of the powder by proton induced X-ray emission gave the following results:

| Wt. % | Elemental Oxide |
|---|---|
| 43.99 | $Al_2O_3$ |
| 50.14 | $ZrO_2$ |
| 1.07 | $HfO_2$ |
| 4.79 | $Y_2O_3$ |
| 99.99 | Total |

X-ray diffraction of the calcined powder showed complete dissolution of the alumina in zirconia and that only crystalline tetragonal zirconia was apparent (see Example 8c). Furthermore yttria stabilized the zirconia into the tetragonal phase. The density, flow, phase and chemical composition of this powder suggested its applicability for plasma spray coating as a thermal barrier and wear resistant coating.

EXAMPLE 3

This Example describes the reaction of acetic acid and zirconium butoxide. The product is an intermediate compound that can be used in forming Zr-O-Al precursors. A 262.8 gm zirconium n-butoxide.butanol complex, 0.5 mole, was mixed with 60 gm of acetic acid, 1 mole, and the mixture Was heated to 80° C. A liquid was distilled off and identified by GC as containing n-butanol and n-butyl acetate. A viscous gel-like product remained. The molecular formula of the product is represented by the unit:

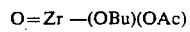

O=Zr —(OBu)(OAc)

The chemical composition of the product was determined by elemental analysis:

| Found %: | C = 31.45 | Calculated: | C = 30.10 |
|---|---|---|---|
|  | H = 4.20 |  | H = 5.02 |
|  | Zr = 37.1 |  | Zr = 38.13 |

The infra red spectra of the product showed a band at 1575 cm$^{-1}$, characteristic of acetate ion, and two bands at 1100 and 150 cm$^{-1}$ characteristic of a butoxyl group.

EXAMPLE 4

Example 4 is similar to Example 3 except that one more mole of acetic acid was added making the ratio of Zr(alkoxide)₄ to acetic acid 1:4. The reaction mixture was dissolved in 300 cc toluene and was heated to 70°–80° C. Distillate (394.4 gm) was then distilled off. GC analysis of the distillate showed it to contain n-butanol, butyl acetate, and toluene.

The chemical composition of the product was found to correspond to the formula Zr(OAc)₄ as follows:

| Found %: | C = 30.65 | Calculated: | C = 29.36 |
|---|---|---|---|
|  | H = 5.61 |  | H = 3.67 |
|  | Zr = 28.7 |  | Zr = 27.87 |

The infra red spectra of the product showed the 1550 cm$^{-1}$ band characteristic of the acetate and no bands for the butoxy group.

EXAMPLE 5

The product obtained from Example 4 was mixed with 253.95 gm of Al sec-(butoxide)₃, 1 mole, and was heated to 85° C. A clear liquid was formed. Upon distillation, sec-butyl acetate and sec-butanol were detected by GC. The chemical analysis of residue was found to correspond to the formula $$\overset{O}{\underset{(BuO)AlOZrOAl(OBu)}{\diagup \diagdown}}$$
(II)

| Found %: | C = 27.16 | Calculated: | C = 27.03 |
|---|---|---|---|
|  | H = 5.40 |  | H = 5.07 |
|  | Zr = 24.30 |  | Zr = 25.68 |
|  | Al = 15.1 |  | Al = 15.2 |

The removal of the sec-butyl acetate from the reaction mixture of Zr(OAc)₄ from Example 4 and aluminum sec-butoxide, above, suggests the linkage of the zirconium and aluminum into one compound. This is further confirmed by the good fit of the above elemental analysis.

EXAMPLE 6

This Example describes the hydrolysis of the compound prepared in Example 1 and further confirms its composition. Compound (I) 50 gms, was dissolved in 1000 cc toluene and 20 gms of water was added. The mixture was stirred at room temperature for three hours. A precipitation of basic acetate was formed. It was filtered and dried at 120° C. for sixteen hours.

Two moles of butanol per one mole of compound I were detected in the filtrate by GC analysis.

The basic acetate was calcined at 1500° C. The oxide formed was analyzed by X-ray diffraction analysis and found to contain crystalline zirconia. No alumina lines were detected indicating that the alumina formed a uniform solid solution where Al and Zr are homogeneously mixed on the molecular level. A manually thoroughly blended mixture of $ZrO_2$ and $Al_2O_3$ in a 1:1 molar ratio and calcined at 1300° C. and 1500° C. showed two separate lines for $ZrO_2$ and α-alumina, the species usually present at temperature greater than 1100° C. This will be summarized in Example 8a and 8b.

EXAMPLE 7

The precursor prepared in Example 5 was hydrolyzed to give the basic bimetallic salt. Initially, 50 gm of the butoxide Zr-Al precursor was dissolved in 1000 cc toluene. Then, 20 cc of water was added while stirring. A transparent gelatinous product was obtained. The addition of a few cc of acetone helped agglomerate the precipitate to a white powder. By evaporating the solvent, a white powder was obtained. It was dried at 120° C. over two hours to yield 36 gm of dried product. GC analysis of the filtrate showed it to contain sec-butanol.

The powder was calcined at 1100° and 1300° C. and XRD analysis found it to contain crystalline $ZrO_2$ and no $Al_2O_3$.

Elemental analysis by proton induced X-ray emission gave the following results:

| Wt. % | Elemental Oxide |
| --- | --- |
| 48.74 | $Al_2O_3$ |
| 50.10 | $ZrO_2$ |
| 1.07 | $HfO_2$ |

EXAMPLE 8

This Example shows that calcined metal oxides prepared from the hydrolysis of Precursor I, Example 1 and Precursor II, Example 5 as described in Examples 6 and 7 respectively are uniform. X-ray diffraction patterns showed $ZrO_2$ exclusively, no alumina phases. Alumina forms a solid solution equally distributed and evenly dispersed in the zirconia phases. It also shows that the addition of yttria would stabilize the $ZrO_2$ in the tetragonal phase.

| Hydrolyzed Precursor | Calcination Temperature | | |
| --- | --- | --- | --- |
|  | 1100° C. | 1300° C. | 1500° C. |
| a) Example 6 and 7 | T $ZrO_2$ | m $ZrO_2$ | m $ZrO_2$ |
| b) Blend of $Al_2O_3$ and $ZrO_2$ | m $ZrO_2$ | m $ZrO_2$ + $Al_2O_3$ | m $ZrO_2$ + $Al_2O_3$ |
| c) Example 2 Zr/Y/Al oxides | T $ZrO_2$ | T $ZrO_2$ | T $ZrO_2$ |

T = tetragonal
m = monoclinic

EXAMPLE 9

The powder from Example 2 was successfully plasma sprayed using a 3 MD Metco Gun over a steel substrate.

Deposition efficiency (DE%) was determined by comparing the coating deposition rate per minute to the powder feed rate per minute. The coating was applied to a 0.5-in ×2-in steel plate for 30 seconds without overspraying, and the weight difference of the plate before and after spraying was compared to the powder feed rate for 30 seconds. Surface roughness was measured using a profilometer on sprayed coating surfaces. Surface profile was directly related to the powder particle size. Coating density was measured by using an image analyzer which optically calculates the porosity percentage within the coatings. A standard ASTM C633-69 Tensile Adhesion Test (TAT) was conducted on the coated samples. Coatings were applied to a TAT stud and then joined to a blank stud, using a heat-cured epoxy. The studs were then pulled apart and the load and mode of failure was recorded. Coating samples of each powder were sprayed to a thickness of approximately 0.020 in. ($\sim 5.1 \times 10^2$ cm). Samples were polished down to 600 grit. Superficial hardness tests were made under 15 kg load. Twelve readings were taken. The high and low values were eliminated and an average was taken.

| | |
| --- | --- |
| DE | = 68.5% |
| Surface roughness | = 350–500 microinches |
| Coating density | = approximately 95% |
| Tensile Strength | = 5179 psi |
| Hardness | = 90 Brale 15 N scale |

These properties suggest that the powder can be used both as a thermal barrier with good porosity and adhesion, as demonstrated by the tensile strength, and also as a wear resistant coating of desirable hardness.

I claim:

1. A process for forming a mixed bimetallic alkoxide-carboxylate composition which comprises reacting at least two different metal alkoxides and a carboxylic acid under substantially anhydrous conditions with elimination of distillable ester by-product therefrom.

2. A process as claimed in claim 1 wherein at least one metal is a tetravalent transition metal.

3. A process as claimed in claim 1 wherein at least one metal is a trivalent transition metal.

4. A process as claimed in claim 1 wherein the transition metal is selected from the group consisting of aluminum, yttrium and zirconium.

5. A process as claimed in claim 1 wherein the metals are tetravalent and trivalent metals in a ratio of from about 1:10 to 10:1.

6. A process as claimed in claim 1 wherein the process is conducted in an organic solvent.

7. A process as claimed in claim 1 wherein the carboxylic acid is acetic acid.

8. A process as claimed in claim 5 wherein yttrium and zirconium are present as the metals.

9. A process as claimed in claim 1 where the process is conducted in the substantial absence of solvent.

10. A process as claimed in claim 1 where the process is conducted in a non-polar solvent.

11. A process as claimed in claim 8 wherein the yttrium to zirconium molar ratio varies from about 1:10 to about 10:1.

12. A process as claimed in claim 1 wherein the mixed metal alkoxide composition is hydrolyzed with water in a non-aqueous solvent to yield a powder which after calcination is suitable for ceramic plasma spray coatings.

13. A novel mixed heavy metal alkoxide carboxylate having the formula

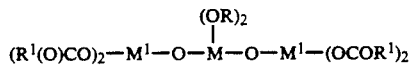

where M is a tetravalent heavy metal, $M^1$ is a trivalent heavy metal, R is alkyl and $R^1$ is lower alkyl.

* * * * *